US012213698B2

(12) United States Patent
Higgins et al.

(10) Patent No.: US 12,213,698 B2
(45) Date of Patent: Feb. 4, 2025

(54) SYSTEMS, METHODS AND DEVICES FOR REMOVAL OF THROMBUS AND/OR SOFT PLAQUE WITH ASYMMETRIC MASS DISTRIBUTION WITHIN WORKING REGION OF IMPELLER

(71) Applicant: Cardiovascular Systems, Inc., St. Paul, MN (US)

(72) Inventors: Joseph P. Higgins, Minnetonka, MN (US); Nicholas W. Rydberg, Stillwater, MN (US); Matthew D. Cambronne, North Oaks, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 98 days.

(21) Appl. No.: 18/070,753

(22) Filed: Nov. 29, 2022

(65) Prior Publication Data
US 2023/0093602 A1 Mar. 23, 2023

Related U.S. Application Data

(62) Division of application No. 17/407,468, filed on Aug. 20, 2021, now Pat. No. 11,523,841.

(60) Provisional application No. 63/073,969, filed on Sep. 3, 2020.

(51) Int. Cl.
*A61B 17/3207* (2006.01)
(52) U.S. Cl.
CPC ............. *A61B 17/320758* (2013.01); *A61B 2017/320766* (2013.01); *A61B 2017/320775* (2013.01)

(58) Field of Classification Search
CPC .... A61B 17/320758; A61B 17/320725; A61B 17/32075; A61B 17/320783; A61B 2017/320766; A61B 2017/320775
See application file for complete search history.

(56) References Cited

U.S. PATENT DOCUMENTS

| | | | |
|---|---|---|---|
| 6,454,775 B1 | 9/2002 | Demarais et al. | |
| 2006/0229659 A1 | 10/2006 | Gifford et al. | |
| 2010/0198239 A1 | 8/2010 | McBroom et al. | |
| 2010/0292720 A1* | 11/2010 | Thatcher | A61B 17/320758 606/159 |
| 2017/0071624 A1 | 3/2017 | McGuckin, Jr. et al. | |
| 2018/0235653 A1 | 8/2018 | Higgins et al. | |

OTHER PUBLICATIONS

International Preliminary Report on Patentability issued in PCT application No. PCT/US2021/047118, dated Mar. 7, 2023.
International Search Report and Written Opinion issued in PCT application No. PCT/US2021/047118, dated Dec. 6, 2021.

* cited by examiner

*Primary Examiner* — Tuan V Nguyen
(74) *Attorney, Agent, or Firm* — Kagan Binder, PLLC

(57) ABSTRACT

A thrombectomy system is provided that, in various embodiments, a rotating impeller that may be translated within limits along a guidewire and within a catheter. The rotating impeller is, during operation, either located entirely inside or outside of the distal end of the catheter's lumen or at least partially outside of the distal end of the catheter's lumen. In some cases, the impeller may be prevented from rotating if at least partially inside the catheter's lumen. The rotating impeller may achieve a working diameter that is greater than its resting diameter.

6 Claims, 5 Drawing Sheets

SYSTEMS, METHODS AND DEVICES FOR REMOVAL OF THROMBUS AND/OR SOFT PLAQUE WITH ASYMMETRIC MASS DISTRIBUTION WITHIN WORKING REGION OF IMPELLER

CROSS-REFERENCE TO RELATED APPLICATIONS

This application is a divisional of U.S. Non-Provisional patent application Ser. No. 17/407,468, filed Aug. 20, 2021 and entitled Systems, Methods and Devices for Removal of Thrombus and/or Soft Plaque with Asymmetric Mass Distribution Within Working Region of Impeller and claims the benefit of U.S. Provisional Application No. 63/073,969, filed Sep. 3, 2020 and entitled Systems, Methods and Devices for Removal of Thrombus and/or Soft Plaque With Asymmetric Mass Distribution Within Working Region of Impeller, the entire contents of which are hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to systems, devices and methods for removing thrombus and soft plaque material in an anatomical conduit. More specifically, a thrombectomy device and method that may be used in conjunction with adjunctive devices and methods such as atherectomy and/or angioplasty.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

In many cases, thrombus and/or soft plaque material must be removed. The presently described invention enables such removal and may be used in conjunction with an exchangeable handle or cartridge and adjunctive procedures such as, e.g., atherectomy and/or angioplasty procedures using the same exchangeable handle or cartridge.

Current thrombectomy devices tend to simply use suction to draw particles through a generic catheter. Often, these catheters become clogged with even moderately sized thrombus particles. Unclogging with current suction-based systems means using high pressure to dislodge the particles. This, in turn, leads to high levels of blood loss and added procedural risks.

In addition, current devices comprise symmetrical mass distribution in the general vicinity of the impeller or propeller, wherein a center of mass of the impeller or propeller is effectively on the rotational axis of the impeller or propeller. As a result, the working diameter of the impeller or propeller achieved during rotation is effectively the same as the resting diameter of the impeller or propeller.

Various embodiments of the present invention address these, inter alia, issues by, among other things, enabling a much lower aspiration pressure while allowing the physician to keep the device tip clear from clogging and enabling treatment of larger and longer regions or areas of thrombus or soft plaque and by enabling a larger working diameter and area for the rotating impeller or propeller. In addition, the larger working diameter occurs as the rotating impeller takes an "orbiting" path relative to the nominal resting or non-orbiting axis of rotation.

BRIEF SUMMARY OF THE INVENTION

A thrombectomy system is provided that, in various embodiments, a rotating impeller that may be translated within limits along a guidewire and within a catheter. The rotating impeller may be attached at, or near, a distal end of the drive shaft which rotates the impeller in response to a prime mover actuation. The impeller may comprise a center of mass that is radially spaced away from the nominal axis of rotation, causing the impeller to achieve a working diameter that is greater than its resting diameter. Alternatively, the system may comprise a radially offset center of mass that also results in the impeller achieving a working diameter that is greater than its resting diameter. Still more alternatively, the surface area of at least part of one blade of the impeller may be larger than other parts of the blade(s).

The figures and the detailed description which follow more particularly exemplify these and other embodiments of the invention.

DETAILED DESCRIPTION OF THE INVENTION

Figure 1:
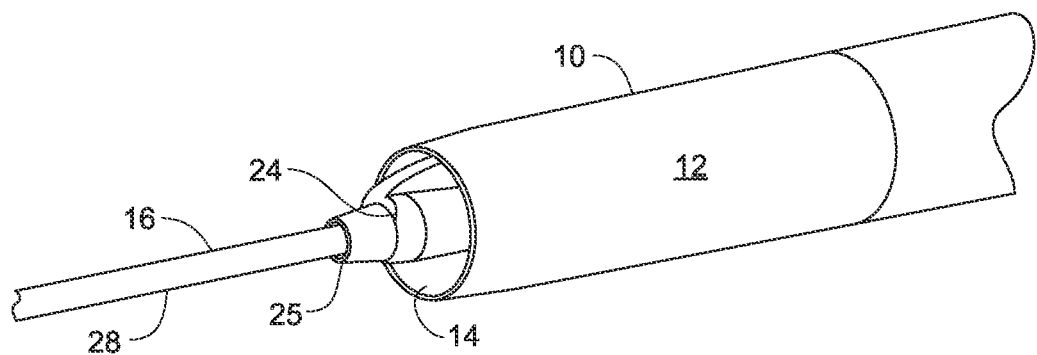
FIG. 1 is a perspective view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

With reference to the Figures, one embodiment of the present invention comprising a catheter 10 having a body 12 with a distal end 15 and defining a lumen 14 therethrough. An impeller device 16 that is rotatable and translatable with a drive shaft within catheter lumen 14 is provided and comprises a tubular shaft 18 defining a proximal end 20, a distal end 22 and an impeller 24 attached at or near the distal end 22 of the tubular drive shaft 18. A guidewire lumen 26 is defined through the impeller device, i.e., through the tubular drive shaft 18 and, in some cases, through the impeller 24 attached at or near the distal end 22 of the tubular drive shaft 18. The guidewire lumen 26 is adapted to receive a guidewire 28 therethrough, thereby enabling the impeller device 16 to be rotated as well as translated over the guidewire 28 and through the catheter lumen 106 to the treatment area in a blood vessel.

The impeller device 16 in FIG. 1 may be locked in place relative to the distal end 22 of the catheter body and the distal end of the catheter lumen 14, with a distal portion of the impeller 24 extending distally from of the distal end 22 of the catheter body 12, i.e., extending partially outside of the catheter lumen 106 to allow, inter alia, easy catheter insertion and enabling breakup of thrombus and/or soft plaque during insertion by rotating the impeller 24 during insertion and positioning of the catheter 12 and impeller device 16 to the location of interest.

Alternatively, the impeller 24 may be rotated when completely within the catheter lumen 14.

Figure 4:
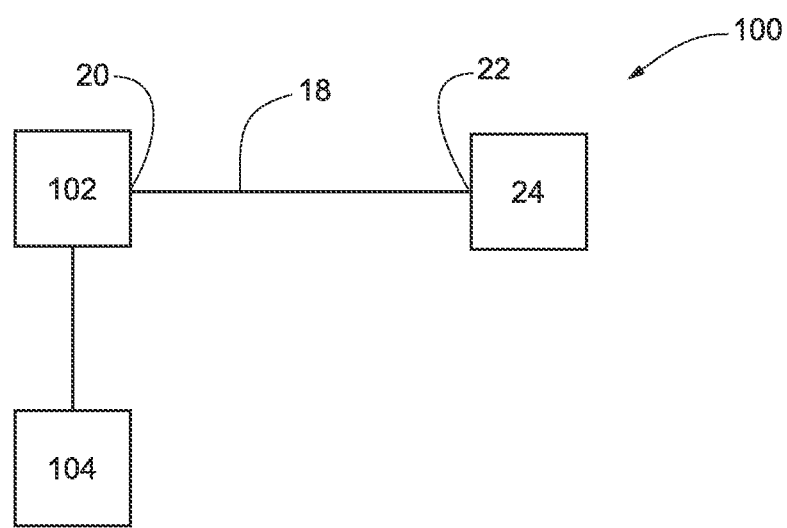
FIG. 4 is a schematic diagram of one embodiment of the present invention.

FIG. 4 illustrates a block schematic diagram of one embodiment of a thrombectomy system 100 comprising a prime mover 102, e.g., an electric motor or turbine or the equivalent in operative communication with a controller 104 comprising a processor in communication with a memory and a display and a data input such as a keyboard as is well known in the art. The prime mover 104 is in rotational connection with the tubular drive shaft 18 of the impeller device 16 which is, in turn, in attached communication with the impeller 24 as described above. The controller 104 comprises executable instructions stored therein, e.g., within the memory, that are executed by the processor. The executable instructions comprise at least (1) information about the length of the tubular shaft that is extended from the prime mover; (2) the distance of the distal tip 25 of the impeller 24 from the prime mover 102 along the tubular drive shaft 18; (3) instructions to prevent rotation of the prime mover 102, and thus the tubular drive shaft 18 and proximal end 20 of impeller 24 operatively attached thereto, if the position of distal tip 25 of the impeller 24 within the lumen 106 of the catheter is completely within the lumen 106 and, therefore, does not extend beyond the distal end 15 of the catheter body 12; and (4) instructions to allow rotation of the prime mover 102, tubular shaft drive 18 and impeller 24 only if at least a portion of the impeller 24 extends distally away from the distal end 15 of the catheter body 10 and, therefore extending at least partially out of the catheter lumen 106.

Thus, under the above control scheme, the embodiment in FIG. 1, with the impeller 24 at least partially extending distally beyond the catheter body 10 may, according to the above instructions, be allowed to rotate by the executable instructions of the controller 104.

Other embodiments may be allowed to rotate when actuated, regardless of the position of the impeller 24 relative to the distal end 15 of catheter body 10.

The impeller 24 may comprise an elongated screw, or helical blade, structure 110 near or at its distal end that may have at least one elongated thread-like structure designed to macerate thrombus and/or soft tissue while also drawing the tissue/thrombus proximally toward the catheter where it may be aspirated therethrough. In some cases, as in, e.g., FIG. 5, an exemplary blade structure 110 may comprise two helical structures 110A and 110B.

Figure 2:
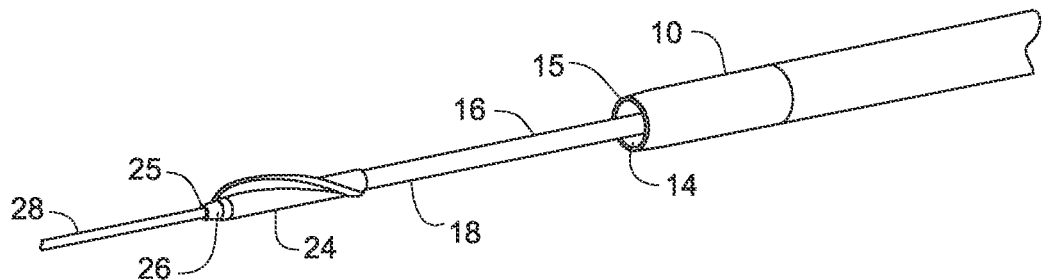
FIG. 2 is a perspective view of one embodiment of the present invention.

FIG. 2 illustrates the impeller device 16 and specifically the impeller 24 as translated distally out and away from the distal end 15 of the catheter 12 where it may macerate or break up soft plaque and/or thrombus, pulling it proximally after breakup toward the distal opening and lumen of the catheter for aspiration with continued rotation so long as at least a part of the impeller remains extended distally beyond the distal end 15 of the catheter 12 or catheter body 10.

Figure 3:
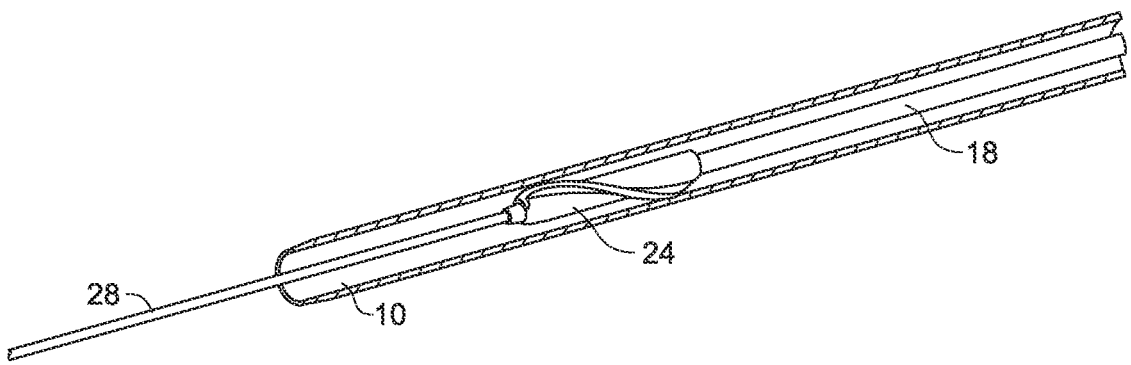
FIG. 3 is a perspective partial cutaway view of one embodiment of the present invention.

FIG. 3 illustrates the impeller device 16, including the impeller 24 positioned as translated proximally entirely within the lumen 14 of the catheter 12, with the impeller 24 spaced proximally from the distal end of the catheter. In certain embodiments, the executable instructions of the controller 104 may prevent the impeller 24 from rotating.

FIGS. 5-10 illustrate exemplary ways that the center of mass of the working region, including the impeller, impeller hub and drive shaft on the proximal and/or distal side of the impeller hub, may be radially offset from the nominal axis of rotation of the drive shaft and working region. The skilled artisan will recognize that some, or all, of the various mechanisms for shifting the center of mass CM radially relative to the axis of rotation AR may stand alone, or may be combined in various ways to achieve the desired result.

As noted above, shifting the center of mass M of the working region allows achieving of a working diameter (generally WD) for the impeller during rotation that is greater than its resting diameter RD which is advantageous.

The Figures disclose exemplary mechanisms to shift the center of mass of the working region radially away from the nominal axis of rotation by (1) creating a mass differential between, or along at least a portion of, the impeller blades, e.g., 110, or 110A, 110B (wherein a one or a plurality of blades are disposed along or around the impeller hub 112); (2) creating a mass imbalance along, or within, the impeller hub 112; and/or (3) creating a mass imbalance along, or within, the tubular drive shaft 18 proximal and/or distal and/or within the impeller hub 112.

Figure 5:
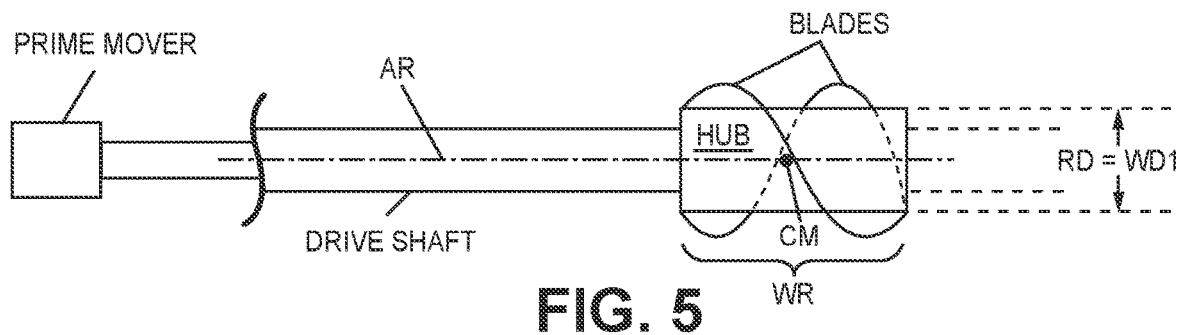
FIG. 5 is a side view of one embodiment of the present invention.

As seen in FIG. 5, the impeller hub 112 with, in the embodiment shown two blades 110A, 110B. The hub 112 is disposed along the tubular drive shaft 18 and, in some embodiments (as shown) the drive shaft 18 extends both proximally and distally away from the impeller hub 112, and extends through a drive shaft lumen (not shown in the Figures) defined by the impeller hub 112. In other cases, the impeller hub 112 may be affixed to, and may extend distally beyond in some embodiments, the distal end of the tubular drive shaft 18, but the lumen through the impeller hub 112 remains to allow a guidewire to pass therethrough.

The nominal axis of rotation AR of the drive shaft and working region WR is shown in FIG. 5's "balanced" configuration with the center of mass CM of working region WR located on the axis of rotation AR. Thus, as shown, the resting diameter RD (measured from radial-most position of the blade(s) 110, or 110A, 110B when at rest of the working region WR is equal to the working diameter WD1, measuring radial-most position of the blade(s) 110, 110A, 110B achieved by the balanced system during rotation. Working region WR may comprise the region covered by the impeller hub 112 in some embodiments or the blade(s) 110, or 110A, 110B in other embodiments. In this embodiment, absent other influences, the resting diameter RD and the working diameter WD are substantially equal.

Figure 6:
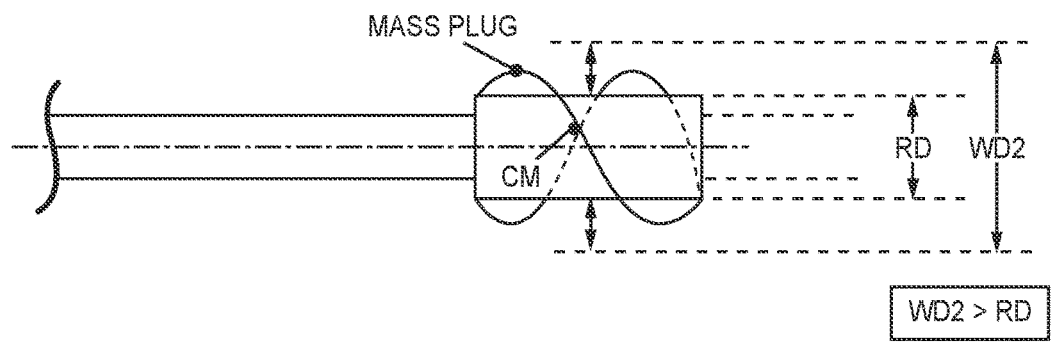
FIG. 6 is a side view of one embodiment of the present invention.

FIG. 6 illustrates one embodiment comprising manipulation of the mass of the impeller and/or impeller blade(s) 110A, 110B to create an imbalance and to shift the working region's center of mass CM radially away from the nominal axis of rotation AR. Accordingly, at least one mass plug 116 of greater density than the blade material may be added along at least one of blades 110A, 110B. Alternatively, at least a portion of at least one blade 110A, 110B may be constructed with a higher density material to create the required mass imbalance. In the embodiment comprising a single helical blade, e.g., 110, at least one mass plug 116 may be disposed along the blade 110 to create the required mass imbalance. Alternatively mass plug 116 may comprise a lower density material than the remaining blade(s) to create the require mass imbalance.

Still more alternatively, the surface area of at least a portion of at least one blade 110, or 110A, 110B, may be increased, relative to other blade surface area portions, to achieve the mass imbalance. In this case, the larger surface area portion(s) of the at least one blade may act to "lift" the impeller through the fluid to create a larger working diameter, taking advantage of the underlying fluid dynamics. The larger surface area portion may, or may not, comprise a larger mass relative to the non-enlarged surface area portion (s) Such structures result generally (as shown) in a working diameter WD2 for the working region WR that is greater than its resting diameter RD during rotation of the drive shaft 18 and hub 18 with blade(s). Alternatively, the surface area of at least a portion of at least one blade(s) may be decreased to achieve the mass imbalance.

Thus, in certain embodiments, in order to create a working diameter WD that is greater than a resting diameter RD:

the mass of at least a portion of one blade may be increased relative to the remaining portion of the at least one blade, and/or increased relative to another blade;

the mass of at least a portion of one blade may be decreased relative to the remaining portion of the at least one blade, and/or decrease relative to another blade;

the density of at least a portion of one blade may be increased relative to the remaining portion of the at least one blade, and/or increased relative to another blade;

the density of at least a portion of one blade may be increased relative to the remaining portion of the at least one blade, and/or increased relative to another blade;

the surface area of at least a portion of one blade may be increased relative to the remaining portion of the at least one blade, and/or increased relative to another blade; and the surface area of at least a portion of one blade may be increased relative to the remaining portion of the at least one blade, and/or increased relative to another blade.

One or more of the above may be combined to achieve the desired mass imbalance.

In each of the cases where a mass imbalance is created, the center of mass CM of working region WR is radially offset from the axis of rotation AR as shown in FIGS. 5 and 6. The degree of offset from the axis or rotation AR may be increased or decreased by increasing the mass, or number of mass plugs 116 and/or increasing or decreasing the surface area or the portion of surface area increased, relative to the remaining blade portions.

Figure 7:
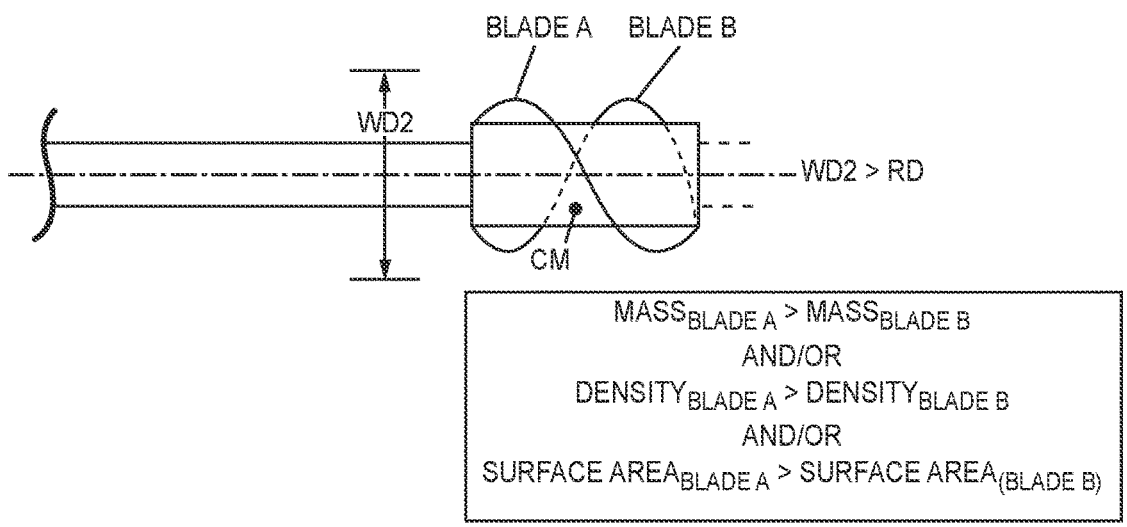
FIG. 7 is a side view of one embodiment of the present invention.

FIGS. 6 and 7 thus illustrates various mechanisms to create the require mass imbalance in the blade(s) 110, or 110A, 110B, wherein the mass/density and/or surface area may be manipulated to move the center of mass CM radially away from the nominal axis of rotation AR.

The skilled artisan will recognize that one of the key features illustrated in FIGS. 6 and 7 is the creation of mass imbalance within or along at least one blade of the working region WR to effect movement of the working region's center of mass CM to shift radially away from the nominal axis of rotation AR. Accordingly, the artisan will recognize equivalent variations to achieve this goal, each of which are within the scope of the present disclosure.

Alternatively, the enlarged surface area portion of at least a portion of at least one of the blades may comprise a material, or a thickness, that allows the resting CM to remain on the nominal axis of rotation AR. In this embodiment, it is the enlarged surface area that, during rotation, works to "lift" the impeller and move it through the fluid and around the nominal axis of rotation AR in an orbiting path. Thus, in this embodiment, the working diameter achieved during orbiting pathing will be larger than the impeller's resting diameter when measured at its largest point.

Figure 8:
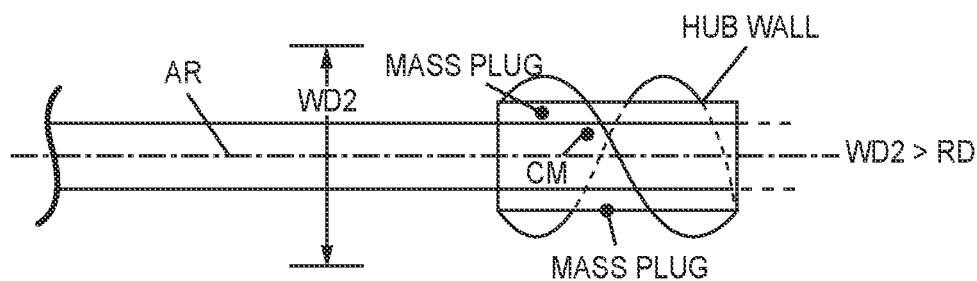
FIG. 8 is a side view of one embodiment of the present invention.
Figure 9:
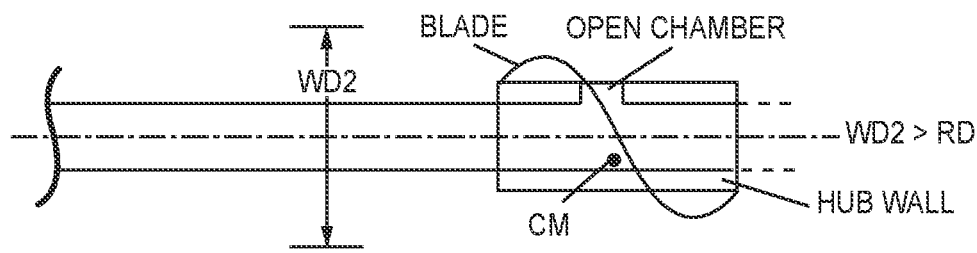
FIG. 9 is a side view of one embodiment of the present invention.
Figure 10:
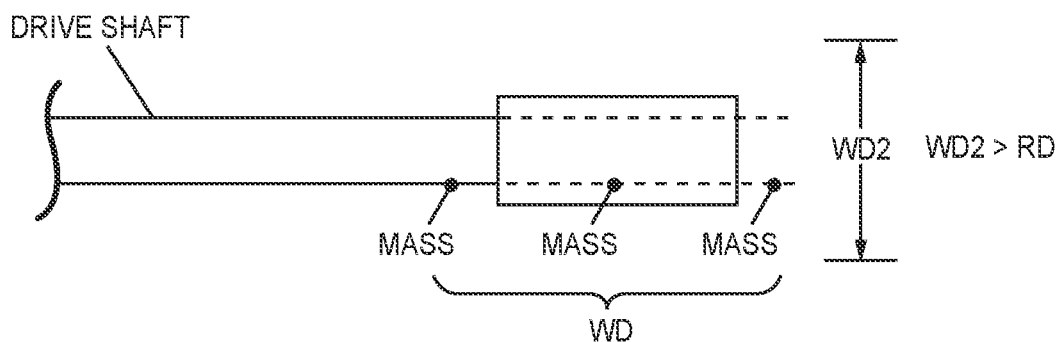
FIG. 10 is a side view of one embodiment of the present invention.

Turning now to FIGS. 8-10, embodiments creating the desired mass imbalance are shown, but in contrast to FIGS. 6 and 7, the mass imbalance is created on (or near) the hub 112 within a working region WR. Stated differently, the center of mass CM of the working region WR is achieved by creating an asymmetrical mass distribution around and/or along the impeller hub 112 and/or the tubular drive shaft 18 near the hub 112.

Thus, as in FIG. 8, a mass plug 116 of density greater than the remainder of the impeller hub 112 material may be used, either along the outside, or inside, or within, the impeller hub 112. Alternatively, a portion of the impeller hub 112 may comprise a material that is more dense than the remaining impeller hub material and that is integrated into the impeller hub 112.

FIG. 9 illustrates removal of a portion, shown as an open chamber within the wall of the impeller hub 112, to achieve the desired mass imbalance and resulting working diameter WD2 which is greater than the resting diameter RD of the working region WR. The shape and size or area of the open chamber, and or more than one spaced-apart open chamber, may be shaped and sized to fit the desired functionality as the skilled artisan will now appreciate.

FIG. 10 also illustrates shifting the center of mass CM of the working region WR radially away from the nominal axis of rotation AR to enable the working region WR achieving a working diameter WD2 that is greater than its resting diameter RD during rotation. In the illustrated example, the drive shaft of the working region WR comprises a mass differential, achieved by, e.g., inserting a wire filar W' in the drive shaft 18 that is at least along a portion of its length is of higher density than the remaining wire filars within the working region WR.

Alternatively, inserting a plug 116 of higher density, and/or by inserting a plug of lower density along the drive shaft, and/or on a wire filar W, at a point within the working region WR that is proximal and/or distal and/or within the impeller hub of the working region WR. Each of these mechanisms will shift the center of mass CM radially away from the nominal axis of rotation.

The above comprise representative examples only. Additional equivalent methods and mechanisms for shifting the center of mass CM of a working region WR of an impeller radially away from a nominal axis of rotation AR during rotation are also within the scope of the present disclosure.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 9,468,457, "ATHERECTOMY DEVICE WITH ECCENTRIC CROWN";
U.S. Pat. No. 9,439,674, "ROTATIONAL ATHERECTOMY DEVICE WITH EXCHANGEABLE DRIVE SHAFT AND MESHING GEARS";
U.S. Pat. No. 9,220,529, "ROTATIONAL ATHERECTOMY DEVICE WITH ELECTRIC MOTOR";
U.S. Pat. No. 9,119,661, "ROTATIONAL ATHERECTOMY DEVICE WITH ELECTRIC MOTOR";
U.S. Pat. No. 9,119,660, "ROTATIONAL ATHERECTOMY DEVICE WITH ELECTRIC MOTOR";
U.S. Pat. No. 9,078,692, "ROTATIONAL ATHERECTOMY SYSTEM";
U.S. Pat. No. 6,295,712, "ROTATIONAL ATHERECTOMY DEVICE";
U.S. Pat. No. 6,494,890, "ECCENTRIC ROTATIONAL ATHERECTOMY DEVICE";
U.S. Pat. No. 6,132,444, "ECCENTRIC DRIVE SHAFT FOR ATHERECTOMY DEVICE AND METHOD FOR MANUFACTURE";
U.S. Pat. No. 6,638,288, "ECCENTRIC DRIVE SHAFT FOR ATHERECTOMY DEVICE AND METHOD FOR MANUFACTURE";
U.S. Pat. No. 5,314,438, "ABRASIVE DRIVE SHAFT DEVICE FOR ROTATIONAL ATHERECTOMY";
U.S. Pat. No. 6,217,595, "ROTATIONAL ATHERECTOMY DEVICE";
U.S. Pat. No. 5,554,163, "ATHERECTOMY DEVICE";
U.S. Pat. No. 7,507,245, "ROTATIONAL ANGIOPLASTY DEVICE WITH ABRASIVE CROWN";
U.S. Pat. No. 6,129,734, "ROTATIONAL ATHERECTOMY DEVICE WITH RADIALLY EXPANDABLE PRIME MOVER COUPLING";
U.S. patent application Ser. No. 11/761,128, "ECCENTRIC ABRADING HEAD FOR HIGH-SPEED ROTATIONAL ATHERECTOMY DEVICES";
U.S. patent application Ser. No. 11/767,725, "SYSTEM, APPARATUS AND METHOD FOR OPENING AN OCCLUDED LESION";
U.S. patent application Ser. No. 12/130,083, "ECCENTRIC ABRADING ELEMENT FOR HIGH-SPEED ROTATIONAL ATHERECTOMY DEVICES";
U.S. patent application Ser. No. 12/363,914, "MULTI-MATERIAL ABRADING HEAD FOR ATHERECTOMY DEVICES HAVING LATERALLY DISPLACED CENTER OF MASS";
U.S. patent application Ser. No. 12/578,222, "ROTATIONAL ATHERECTOMY DEVICE WITH PRE-CURVED DRIVE SHAFT";
U.S. patent application Ser. No. 12/130,024, "ECCENTRIC ABRADING AND CUTTING HEAD FOR HIGH-SPEED ROTATIONAL ATHERECTOMY DEVICES";
U.S. patent application Ser. No. 12/580,590, "ECCENTRIC ABRADING AND CUTTING HEAD FOR HIGH-SPEED ROTATIONAL ATHERECTOMY DEVICES";
U.S. patent application Ser. No. 29/298,320, "ROTATIONAL ATHERECTOMY ABRASIVE CROWN";
U.S. patent application Ser. No. 29/297,122, "ROTATIONAL ATHERECTOMY ABRASIVE CROWN";
U.S. patent application Ser. No. 12/466,130, "BIDIRECTIONAL EXPANDABLE HEAD FOR ROTATIONAL ATHERECTOMY DEVICE"; and
U.S. patent application Ser. No. 12/388,703, "ROTATIONAL ATHERECTOMY SEGMENTED ABRADING HEAD AND METHOD TO IMPROVE ABRADING EFFICIENCY".

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A thrombus disruption and removal system, comprising:
   a drive shaft defining a proximal end and a distal end and an axis of rotation;
   a working region defined near, or at, the distal end of the drive shaft, the working region comprising:
   an impeller hub defining a wall and attached to and/or surrounding the drive shaft;
   a plurality of impeller blades attached to, or integrated with, the impeller hub and extending radially therefrom, at least one impeller blade being helical;
   at least a portion of the drive shaft engaging the impeller hub and extending at least partially through a lumen defined through the impeller hub;
   a prime mover coupled to the proximal end of the drive shaft and, together with the drive shaft, configured to rotate the impeller hub and to translate the working region,
   wherein at least one of the impeller blades comprises a surface area that is greater than the surface area of any one of the remaining impeller blades in the plurality of impeller blades.

2. The thrombus disruption and removal system of claim 1, wherein a working diameter of the impeller blades achieved during rotation of the impeller is greater than a resting diameter of the impeller blades.

3. The thrombus disruption and removal system of claim 1, wherein the at least one of the impeller blades comprises a mass that is greater than the mass of any one of the remaining impeller blades in the plurality of impeller blades.

4. The thrombus disruption and removal system of claim 1, wherein at least one of the impeller blades comprising a mass that is greater than the mass of any one of the remaining impeller blades in the plurality of impeller blades and comprises a surface area that is greater than the surface area of any one of the remaining impeller blades in the plurality of impeller blades.

5. A thrombus disruption and removal system, comprising:
- a drive shaft defining a proximal end and a distal end and an axis of rotation;

a working region defined near, or at, the distal end of the drive shaft, the working region comprising:
- an impeller hub defining a wall and attached to and/or surrounding the drive shaft;
- a plurality of impeller blades attached to, or integrated with, the impeller hub and extending radially therefrom, wherein the impeller blades are shaped so as to draw tissue during rotation of the impeller hub proximally from a thrombus;
- at least a portion of the drive shaft engaging the impeller hub and extending at least partially through a lumen defined through the impeller hub;
- a prime mover coupled to the proximal end of the drive shaft and, together with the drive shaft, configured to rotate the impeller hub and to translate the working region,
- wherein at least one of the impeller blades comprises a surface area that is greater than the surface area of any one of the remaining impeller blades in the plurality of impeller blades.

6. The thrombus disruption and removal system of claim 5, further comprising a catheter having a proximal end and a distal end and a lumen within which the drive shaft is rotatable and translatable, wherein the impeller blades, when rotated, further aspirate the tissue from the thrombus within the lumen of the catheter.

* * * * *